United States Patent

Klaveness et al.

[11] Patent Number: 6,110,444
[45] Date of Patent: Aug. 29, 2000

[54] GAS-CONTAINING MICROCAPSULES USEFUL AS CONTRAST AGENTS FOR DIAGNOSTIC IMAGING

[75] Inventors: Jo Klaveness; Balin Balinov, both of Oslo, Norway

[73] Assignee: Nycomed Imaging AS, United Kingdom

[21] Appl. No.: 09/005,758

[22] Filed: Jan. 12, 1998

Related U.S. Application Data

[63] Continuation of application No. 08/467,274, Jun. 6, 1995, abandoned, which is a continuation of application No. PCT/GB95/00437, Mar. 1, 1995.

[30] Foreign Application Priority Data

Mar. 1, 1994 [NO] Norway ..................................... 940711

[51] Int. Cl.$^7$ ............................ A61K 49/04; A61K 9/50; B01J 13/02
[52] U.S. Cl. .......................... 424/9.52; 424/489; 424/499; 264/4.1; 264/4.3; 427/213.3; 427/213.31; 427/213.33; 427/213.35
[58] Field of Search ..................................... 424/9.52, 9.5, 424/9.51, 489, 499; 264/4, 4.1, 4.3, 4.33; 427/213.3, 213.31, 213.35, 213.36, 213.33

[56] References Cited

U.S. PATENT DOCUMENTS

| 5,147,631 | 9/1992 | Glajch et al. ......................... 424/9.52 |
| 5,505,932 | 4/1996 | Grinstaff et al. ....................... 424/9.3 |
| 5,648,095 | 7/1997 | Illum et al. .............................. 424/489 |
| 5,718,884 | 2/1998 | Klaveness et al. .................... 424/9.52 |

FOREIGN PATENT DOCUMENTS 9112823 9/1991 WIPO .............................. A61K 9/50

*Primary Examiner*—José G. Dees
*Assistant Examiner*—Michael G. Hartley
*Attorney, Agent, or Firm*—Bacon & Thomas PLLC.

[57] ABSTRACT

Gas-containing microcapsules useful as imaging agents, e.g. as ultrasound contrast agents, may be prepared by forming a dispersion of gas microbubbles in an aqueous medium comprising a solution or dispersion of a wall-forming material and subsequently inducing direct microencapsulation of these microbubbles by the wall-forming material.

10 Claims, No Drawings

GAS-CONTAINING MICROCAPSULES USEFUL AS CONTRAST AGENTS FOR DIAGNOSTIC IMAGING

This application is a Continuation of nonprovisional application Ser. No. 08/467,274 filed Jun. 6, 1995, now abandoned, which is a Continuation of international application Ser. No. PCT/GB95/00437, filed Mar. 1, 1995.

This invention relates to a novel method for the preparation of gas-containing microcapsules, to novel gas-containing microcapsules obtainable thereby and to contrast agents of use in diagnostic imaging, in particular ultrasound imaging, containing such microcapsules.

It is well known that ultrasonic imaging comprises a promising diagnostic tool, for example in studies of the vascular system, particularly in cardiography, and of tissue microvasculature. It has long been known that it may be advantageous to increase the difference in acoustic properties between different tissues and/or fluids using contrast agents which, when injected into the body, may be carried along e.g. the circulatory system to various organs to be imaged. A variety of contrast agents has been proposed to enhance acoustic images, including suspensions of solid particles, emulsified liquid droplets, free gas microbubbles and encapsulated gases and liquids. It is generally accepted that low density contrast agents which are easily compressible are particularly efficient in terms of the acoustic backscatter they generate. Hence gas-containing contrast agents have attracted particular interest.

Gas-containing contrast media are also known to be effective in diagnostic examinations other than ultrasonic imaging. Thus they are of use in magnetic resonance (MR) imaging, e.g. as susceptibility contrast agents which will act to reduce MR signal intensity. Oxygen-containing contrast media also represent potentially useful paramagnetic MR contrast agents. Furthermore in the field of X-ray imaging it has been observed that gases such as carbon dioxide may be used as negative oral contrast agents.

Initial ultrasound studies involving free gas microbubbles, either preformed in vitro or generated in vivo by intracardiac injection of physiologically acceptable substances, have demonstrated the potential efficacy of such microbubbles as contrast agents in echocardiography; such techniques are severely limited in practice, however, by the short lifetime of the free microbubbles, which rapidly disappear as the gas dissolves in body fluids. Interest has accordingly been shown in developing methods of stabilising gas microbubbles for echocardiography and other ultrasonic studies, for example using emulsifiers, oils, thickeners or sugars, or by entraining or encapsulating the gas or a precursor therefor in a variety of systems, e.g. as porous gas-containing microparticles, or as encapsulated gas microbubbles, conveniently termed microcapsules.

Whilst various ultrasound contrast agents have been proposed which exhibit adequate stability during storage and handling, there is an ongoing need for contrast agents comprising gas-containing microcapsules which are also stable in vivo, preferably for several passages of circulation in the case of intracardiac injections. Previous proposals relating to such ultrasound contrast agents have typically required the use of polymeric or macromolecular encapsulating coatings for the microbubbles, with the intention of preventing the gas from escaping by dissolution and also preventing the microbubbles from coalescing into bubbles of a larger size than that preferred for use in echocardiography (1–10 $\mu$m). Thus, for example, WO-A-8002365 in principle suggests use of microbubbles encapsulated by a coalescence-resistant membrane comprising non-toxic and non-antigenic organic molecules, but in practice discloses only the use of of gelatin for encapsulation. It has been found that microbubbles so encapsulated do not exhibit adequate stability in vivo to allow imaging of the left side of the heart and of the myocardium, which will normally require more than one passage of circulation.

As regards preparation of gas-containing microcapsules, A. Kondo in "Microcapsule Processing and Technology", Marcel Dekker Inc., New York (1979), p.109 suggests forming hollow capsules using a low-boiling solvent as the core and subsequently removing the core.

WO-A-9112823 provides a process for the preparation of gas-containing microcapsules by forming a shell around a solid or liquid core and subsequently removing the core, e.g. by evaporation. The core is preferably a volatile oil such as perfluorohexane. The shell may be made by methods involving simple or complex coacervation, oil-in-water-in-oil double emulsions, or minimisation of solubility at the isoelectric point. The shell may be further hardened chemically or by heat to render it water-insoluble. Microcapsules prepared in this way may be used for echocardiography when subsequently filled with a gas.

U.S. Pat. No. 4,718,433 describes the preparation of ultrasound contrast agents by high frequency sonication and simultaneous heating of an aqueous solution of a protein such as human serum albumin so as to generate gas microbubbles which are stabilised by encapsulation with thermally denatured protein. In many cases heating is directly induced by the sonication so that no extraneous heat source is required.

EP-A-0359246 proposes an improved process for the preparation of such proteinaceous gas-containing microcapsules wherein the protein solution is pre-heated to a temperature of incipient denaturation and is treated with gas prior to sonication. Such pre-heating will inevitably ensure that sonication to promote microbubble formation will be accompanied by sonication-induced thermal denaturation of the protein.

Wheatley et al. in Biomaterials 11 (1990), pp. 713–717 suggest the preparation of ultrasound contrast agents by coextrusion of air and an aqueous solution of sodium alginate to produce nascent microencapsulated air bubbles as individual droplets which fall into a hardening solution containing calcium ions. Such a process will inevitably be difficult to operate on a commercial manufacturing scale; furthermore, the encapsulated microcapsules typically have a size (100±15 $\mu$m) which prohibits their use in applications such as echocardiography EP-A-0398935 discloses ultrasound contrast agents which may be prepared by dissolving a polymer in a solvent containing gas bubbles and then precipitating or emulsifying the product in water. However, the gas bubbles do not appear to be encapsulated by the polymer in this process.

The present invention is based on the finding that gas-containing microcapsules may be effectively and efficiently prepared by forming a dispersion of gas microbubbles in an aqueous medium comprising a solution or dispersion of a wall-forming material and subsequently inducing direct microencapsulation of these microbubbles by the wall-forming material. This process has the advantage that it avoids the need to encapsulate and then remove a precursor solid or liquid core, e.g. as described in the above-mentioned WO-A-9112823, and is therefore markedly simpler to operate. Moreover, the separation of the microbubble-generating and microencapsulation stages, in contrast to procedures such as those described in the above-mentioned U.S. Pat.

No. 4,718,433 and EP-A-0359246, permits greater control over the process and parameters such as the size of the microcapsules which are produced.

Thus according to one aspect of the present invention there is provided a process for the preparation of gas-containing microcapsules which comprises dispersing gas microbubbles in an aqueous solution or dispersion of a wall-forming material and thereafter inducing direct microencapsulation of the resulting gaseous cores by the wall-forming material and separating the formed microcapsules from the said solution or dispersion.

Gas-containing microcapsules obtainable by the above-defined process are themselves novel and constitute a feature of the invention. These microcapsules may be distinguished from gas-containing microcapsules prepared according to the prior art by the absence of residual precursor core materials such as volatile oils and by reduced levels of aggregates such as may be generated by simultaneous foaming and denaturation of protein solutions.

The wall-forming material is preferably a charged group-carrying polymer or macromolecule. Polymers of interest include linear and branched soluble polymers carrying one or more charges per monomer unit, and colloidal polymer particles with a high surface charge density. Macromolecules carrying relatively small numbers of charged groups, such as proteins, in particular albumin and gelatin, are also of interest.

The wall-forming material may, if desired, also comprise, for example, biocompatible metal ions such as $Ca^{2+}$, $Fe^{3+}$ or $Zn^{2+}$, or low molecular weight molecules carrying one or more charges.

Gases which may be present in the microcapsules include any substance which is in gaseous form under normal storage conditions (for example at room temperature) and/or at normal human body temperature. It is therefore generally preferred to employ substances having a liquid to gas transition temperature below 37° C. The gases preferably have low solubility in water to ensure long persistence in the aqueous medium employed during the microencapsulation process. Examples of suitable gases thus include hydrocarbons such as methane and acetylene; halogenated hydrocarbons, such as methyl bromide and, more particularly, fluorinated hydrocarbons such as perfluoroalkanes and perfluorocycloalkanes (e.g. octafluorocyclobutane). The use of perfluorocarbons such as perfluorobutane and perfluoropentane and perfluorinated sulphur compounds such as sulphur hexafluoride and disulphur decafluoride is particularly preferred because of their low solubility in water and lack of toxicity at relevant concentrations. Gases such as air, carbon dioxide, oxygen, nitrogen and argon may also be suitable, as may mixtures of two or more gases, for example perfluropentane and argon.

Compounds such as perfluoropentane may be in the liquid state at certain stages of processing but may be transformed to gas microbubbles in the aqueous processing medium, e.g. by heating, decrease of pressure or application of mechanical shear.

The use of gases with low water solubility constitutes an extra advantage of the invention where the microcapsules are to be used as contrast agents in that the escape of such gases from the microcapsules in an aqueous physiological environment will be greatly delayed. Even after escape of such gases from the microcapsules, they will persist as free gas microbubbles in such an aqueous environment.

Dispersion of the gas to form microbubbles may, for example, be achieved by passing the gas through the polymer solution or dispersion in the form of relatively large bubbles, e.g. of about 1–2 mm in diameter, and then effecting reduction to the desired size by mechanical mixing. The mechanical mixer may, for example, be a commercial high pressure homogenizer or any other mixer capable of forming a gas-in-liquid emulsion in which the microbubble diameter is preferably between 2 and 10 μm (see, for example, Kumar R, Kuluor N in "Advances in Chemical Engineering, ed.T. Drew et al., Vol 8, Acad. Press., London (1970), pp. 265–369). The microbubble dispersion may also readily be formed by injecting gas under pressure or through a porous filter just prior to such mechanical mixing. Aeration machines, e.g. such as are known from classical flotation processes, may also be used to produce fine microbubble dispersions.

It will be appreciated that where heat sensitive wall-forming materials such as proteins are employed, the temperature during dispersion of the gas should be kept sufficiently low to prevent any significant denaturation or other unwanted reactions of the wall-forming material during this stage.

Whilst the wall-forming material will often stabilise the microbubble dispersion it may be advantageous additionally to use one or more suitable surfactants to promote additional stabilisation thereof.

Induction of microencapsulation of the gaseous cores will typically involve decreasing the solubility of the wall-forming material in the aqueous processing medium so as to bring about phase separation whereby wall-forming material deposits around the gas microbubbles; this is commonly termed coacervation. Coacervation processes are widely used for encapsulation of solid and liquid core materials in various applications in the pharmaceutical, food and cosmetic industries (see, for example, the above-mentioned WO-A-9112823 and Reza Arshady, Polymer Engineering and Science, 30 (1990), p.905). Microencapsulation in accordance with the invention may be effected by either simple or complex coacervation. In the former the required phase separation may, for example, be induced by changing the pH or salt content of the aqueous medium, by changing the temperature or by addition of a solvent. Complex coacervation, on the other hand, typically involves addition of a solution of a second polymer or macromolecule which is capable of complexing with the wall-forming material so as to promote microencapsulation of the gaseous cores by a complex mixture of two or more polymers or macromolecules.

When complex coacervation is employed, the two polymers or macromolecules are usually oppositely charged polyelectrolytes which upon mixing will form a polyelectrolyte complex with low solubility in water, leading to coacervation and formation of a protective microencapsulating layer around each microbubble. Suitable polyelectrolytes include, for example, anionic polymers such as polyphosphates (e.g. polyphosphorylated carbohydrates) and polycarboxylates (e.g. polyacrylates and polymethacrylates), which may be combined with cationic polymers such as poly-N-ethyl-4-vinylpyridine or poly-2,5-ionene bromide. Other examples of anionic polymers are polysaccharides and their derivatives such as acacia, carrageenan, agarose, alginic acid and salts thereof, heparin, hyaluronan, pectins and their derivatives such as sodium amylosulphate etc. These may be combined with cationic materials such as chitosan or cationic cellulose derivatives, e.g. from hydroxyethylcellulose, such as Polymer JR (Union Carbide).

Proteins are an important class of biological polyelectrolytes and are especially useful due to their biological acceptability, their ability to be precipitated by heating and their amphoteric character (being positively or negatively charged depending on the pH). For example serum albumin below its isoelectric point (pH=5.1) is positively charged and tends to precipitate in the presence of polyanions, but above the isoelectric point tends to associate with positively charged polymers such as polylysine. Other proteins which may be useful include collagen, gelatin, casein, insulin, fibrinogen etc. Polypeptides such as poly(L-ornithine) are also useful and may be precipitated with negatively charged polyelectrolytes, for example dextran derivatives such as carboxymethyldextran. Block polypeptides such as the anionic poly(alanine-glutamic acid) can also be used to cause coacervation.

Biocompatible low molecular weight ionic substances capable of linking two or more anionic or cationic groups at body pH values may also be used to generate and/or stabilise the microencapsulating layer. Thus metal ions such as $Ca^{2+}$, $Fe^{3+}$ or $Zn^{2+}$ have the ability to bind to two or more anionic groups of a polymer, whilst polyacids such as citric acid or tartaric acid may similarly bind to two or more cationic groups of a polymer.

The addition of surfactants may also be useful to stabilise the microbubbles during coacervation and/or to induce deposition of the wall-forming material around the microbubbles. Thus cationic surfactants such as cetyltrimethyl ammonium bromide may be combined with negatively charged polymers such as dextran derivatives. Anionic surfactants such as sodium dodecyl sulphate may similarly be used with positively charged polyelectrolytes such as gelatin at pHs below its isoelectric point. Nonionic surfactants, e.g. sorbitan monolaurate, may also be useful in combination with the above mentioned wall-forming materials. In all these cases the surfactant constitutes a component of the microencapsulating layer and contributes to the desired decrease in the solubility of the wall-forming material.

After preparation of the microbubble dispersion the precise constitution of the microcapsules which are then formed may be varied widely by selection of appropriate conditions for coacervation. In the case of simple coacervation the microbubble dispersion may, for example, be treated by addition of a salt solution or by changing the pH at an appropriate, e.g. slow, rate while mixing to prevent aggregation of the microcapsules. Temperature is also an important factor and may either be decreased, e.g. to harden the microcapsules or increased, e.g. to denature a wall-forming protein. Where complex coacervation is employed, the microbubble dispersion may be mixed with another polymer or macromolecule solution at an appropriate, e.g. slow, rate. Gradual cooling of the mixture will usually accelerate coacervation, the rate and time of cooling determining the thickness and other physical properties of the encapsulating layer. Additional dilution may be required to prevent aggregation of the microcapsules. Formation of a uniform protective layer may be achieved by selection of optimal process conditions, the mechanical and interfacial properties of the layer being determined by the composition of the ingredients. Thus the required stability of the microcapsules during storage and use, e.g. in medical diagnosis, may be achieved even when the ingredients exhibit substantial solubility in water and body fluids, since the final solubility of the encapsulating layer may be regulated by its final composition. It will be appreciated that the choice of the complexing materials will also be based upon toxicity considerations where medical applications are envisaged.

The encapsulating layer may optionally subsequently be hardened, e.g. by thermal treatment, desolvation techniques, cross-linking or coating with another polymer or macromolecule layer. Such second coating may be effected by further simple or complex coacervation or by immersing the coated microcapsules in a solution of a further polymer or macromolecule capable of forming complexes and penetrating into or depositing on the encapsulating layer. Such hardening of the encapsulating layer may improve properties such as the mechanical resilience and/or biocompatibility of the microcapsules.

Microcapsules prepared as described above may, for example, be separated from the reaction mixture by techniques such as sedimentation, flotation or filtration, e.g. involving continuous or repeated washing. The recovered microcapsules may be stored as a suspension in an appropriate diluent or in dried powder form, e.g. in a closed vessel under a chosen gas atmosphere, which may be the same as or different from the encapsulated gas. In the case of microcapsules intended for use as injectable contrast agents, appropriate diluents for stored suspensions or for reconstitution of dried forms include sterile water, physiological saline and biocompatible buffers, such as phosphate-buffered saline.

Microcapsules obtained in accordance with the invention may also be used for non-medical purposes, e.g. as opacifier systems for use in paints or in papers as described in U.S. Pat. No. 3781230.

Microcapsules in accordance with the invention are particularly useful as imaging contrast agents, e.g. for X-ray and magnetic resonance imaging, and more especially as ultrasound contrast agents.

Thus, in a further aspect of the invention, we provide gas-containing microcapsules as hereinbefore defined for diagnostic imaging, in particular for ultrasound imaging, e.g. for echocardiography, perfusion studies and Doppler ultrasound imaging. It will be appreciated that the encapsulating material in such microcapsules should be both biotolerable and biocompatible; it should preferably also be biodegradable to facilitate subsequent excretion of the contrast agent.

For ultrasonic applications such as echocardiography, in order to permit free passage through the pulmonary system and to achieve imaging at the preferred frequency of about 0.1–15 MHz, the microcapsules employed should preferably have an average size below 10 $\mu$m, e.g. 1–10 $\mu$m, more preferably 1–7 $\mu$m. Microcapsules of susbstantially larger size, e.g. with average size up to 500 $\mu$m, may be useful for other applications, e.g. in gastrointestinal imaging or imaging of the uterus or Fallopian tubes. The following non-limitative Examples further illustrate the present invention.

EXAMPLE 1

Simple Coacervation a) Formation of Gas Microbubbles

Liquid perfluoropentane (0.5 g) was dispersed in an aqueous solution of gelatin (10 wt %, 49.5 g) for 3 minutes at 50° C. under stirring with an Ultra Turrax type laboratory homogenizer (Ystral) at 18,000 rpm. The resulting emulsion contained microbubbles with a size of about 5 $\mu$m, as evidenced by optical microscopy (Axioskop, Zeiss, Germany).

b) Coating of Microbubbles with Gelatin

An aqueous solution of sodium sulphate (20 wt %, 20 g) was added over half an hour to the microbubble dispersion from (a) above while mixing and cooling to 20° C. The resulting gelatin-coated microbubbles were washed three times by dispersing for 5 minutes in aqueous sodium sulphate (7 wt %, 500 ml) at 20° C., allowing the microcapsules to float for 15 minutes, and removing the aqueous solution from the bottom of the vessel. Inspection by microscopy indicated a yield of non-aggregated microcapsules with a diameter from 3 to 10 μm of about 40%. The smaller microcapsules were separated from larger aggregates by mixing the dispersed microcapsules in a 10 cm sedimentation column to obtain a homogeneous mixture, allowing this to settle for one minute and discarding the upper half volume containing mainly large aggregates. The thus-obtained microcapsules mainly had a diameter below 10 μm.

An in vitro ultrasound attenuation of 6 dB/cm was measured as a mean value in the frequency range from 1 to 6 MHz.

EXAMPLE 2
Complex Coacervation

Liquid perfluoropentane (0.5 g) was dispersed in an aqueous solution of gelatin (2%, 49.5 g) for 15 minutes at 50° C. under stirring with an Ultra Turrax type laboratory homogenizer (Ystral) at 25,000 rpm. The resulting emulsion contained microbubbles with a size mainly from 2 to 5 μm as evidenced by optical microscopy. The microbubble dispersion was cooled to 30° C. over 10 minutes and complex coacervation was performed by slowly adding an aqueous solution of acacia (1 wt %, 50 g) whilst gently mixing at 2000 rpm. Microcapsules containing perfluoropentane, with a mean diameter below 8 μm, were formed by cooling the dispersion slowly to 20° C. under continuous mixing for half an hour.

EXAMPLE 3
Simple Heat-induced Coacervation

A solution of human serum albumin in pH 7.2 phosphate-buffered saline (2 wt %, 49.5 g) was used to emulsify perfluoropentane as an oil-in-water emulsion, using an Ultra Turrax type laboratory homogenizer at 5,000 rpm for 5 minutes at approximately 10° C. Subsequently intensive foaming was effected by mixing at 20,000 rpm for 3 minutes at room temperature, giving a viscous concentrated foam. The foam was then mixed with pH 7.2 phosphate-buffered saline (150 ml) at 60° C. to disperse the microbubbles. This dispersion was immediately heated in an microwave oven (800 W) at about 70° C. for about 40 seconds to cause denaturation of the albumin. The sample was then gently mixed for five minutes using a propeller type stirrer to prevent microcapsule aggregation, and heated again to 90° C. by microwave oven for 3 to 5 minutes. Microscopic examination revealed the size of the microcapsules to be mainly from 2 to 15 μm almost without aggregates. Dynamic light scattering (Malvern 1002, UK) revealed a mean diameter of 7.2 μm.

Residual foam and larger microspheres containing perfluoropentane were removed from the microcapsules by the flotation/washing procedure described in Example 1(b) The yield of microcapsules with a size below 10 μm was above 80%.

Acoustic attenuation in the frequency range from 1 to 6 MHz was measured; high echogenicity and good stability of the contrast agent were observed. Thus a mean signal of about 8 dB/cm was observed when the microcapsules were diluted to a concentration of less than 1 vol %. A sample suspension of the microcapsules was stored for 8 weeks at 4° C.; subsequent microscopic examination revealed some disappearance of smaller microcapsules, causing the average size to increase slightly. The in vitro acoustic attenuation of these microcapsules had decreased to about 60% of the initial value. The ratio between the scattering intensity and the attenuation of the stored sample was better than for microspheres prepared analogously to the commercially available Albunex® contrast agent.

EXAMPLE 4
Simple Heat-induced Coacervation

A closed vessel was connected by plastic tube to a cylinder containing pressurised perfluorobutane. The vessel was cooled below −10° C. before transfer of about 1 cm$^3$ of liquid perfluorobutane. The closed vessel was then disconnected from the gas cylinder and the liquid perfluorobutane was mixed and dispersed with an aqueous solution of human serum albumin (2 wt %, 50 ml) at 0° C. A coarse oil-in-water emulsion was formed by shaking the vessel by hand for about 2 minutes. Thereafter a microbubble dispersion was formed and encapsulation was effected with the same procedure and reagent quantities etc. as in Example 3.

EXAMPLE 5
In Vivo Measurements of Acoustic Effects a. Ultrasound Doppler enhancement after intravenous injection of the microcapsule suspension of Example 2 in rabbits gave good arterial and venous Doppler signals with durations of 1 to 2 minutes.

b. Arterial and venous Doppler enhancement of microcapsule suspensions according to Example 3 in rabbits are given in Table 1.

c. In vivo Doppler enhancement of the microcapsule suspension of Example 3 decreased to about 60% after storage for 8 weeks at 4° C. The ratio between the scattering intensity and the attenuation of the stored sample was better than for microspheres prepared analogously to the commercially available Albunex® contrast agent.

d. Myocardial contrast enhancement in dogs was about 40 times grey level after injection with a dose of 0.1 ml/kg of the microcapsule suspension of Example 3.

e. Arterial and venous Doppler enhancement of the microcapsule suspension of Example 4 were tested in rabbits. Values are given in Table 1.

TABLE 1

| | | Artery | | | Vein | | |
|---|---|---|---|---|---|---|---|
| Gas type | Injected vol (ml) | Peak (DU) | Integral (DU.sec) | Duration (sec) | Peak (DU) | Integral (DU.sec) | Duration (sec) |
| Example 3 | | | | | | | |
| F-pentane[1] | 0.5 | 13.9 | 1205 | 358 | 12 | 1766 | 450 |
| F-pentane | 0.2 | 12.2 | 683 | 242 | 8.5 | 792 | 260 |
| Example 4 | | | | | | | |
| F-butane[2] | 0.2 | 12.2 | 886 | 296 | 8.5 | 885 | 305 |

[1]F-pentane = perfluoropentane
[2]F-butane = perfluorobutane

We claim:

1. A process for the preparation of gas-containing microcapsules which comprises dispersing free microbubbles of a substantially water-insoluble gas in an aqueous solution or dispersion of a polymeric or macromolecular wall-forming material and thereafter inducing direct microencapsulation of said microbubbles by the wall-forming material by means of a simple or complex coacervation process, thereby yielding gas-containing microcapsules comprising microbubbles of said gas encapsulated by uniform protective layers of polymeric or macromolecular wall-forming material, and separating said gas-containing microcapsules from the said solution or dispersion.

2. A process as claimed in claim 1 wherein the wall-forming material is a charged group-carrying polymer or macromolecule.

3. A process as claimed in claim 2 wherein the wall-forming material is selected from soluble linear and branched polymers carrying one or more charges per monomer unit, colloidal polymer particles with high surface charge density, and proteins.

4. A process as claimed in claim 3 wherein the wall-forming material is albumin or gelatin.

5. A process as claimed in claim 1 wherein said gas is a fluorinated gas.

6. A process as claimed in claim 5 wherein said gas is selected from perfluorobutane, perfluoropentane, sulphur hexafluoride and disulphur decafluoride.

7. A process as claimed in claim 1 wherein simple coacervation is induced by addition of an aqueous salt solution to the gas microbubble-containing aqueous solution or dispersion of wall-forming material.

8. A process as claimed in claim 1 wherein simple coacervation is induced by heating a gas microbubble-containing aqueous solution or dispersion of a proteinaceous wall-forming material.

9. A process as claimed in claim 1 wherein complex coacervation is induced by addition of a charged polymer to a gas microbubble-containing aqueous solution or dispersion of a wall-forming material of opposite charge.

10. A process as claimed in claim 1 wherein the microcapsules are subsequently stabilised by thermal treatment, desolvation, crosslinking or coating with a further polymer layer.

* * * * *